United States Patent
Weibel et al.

(10) Patent No.: US 6,710,050 B2
(45) Date of Patent: Mar. 23, 2004

(54) PHARMACEUTICAL COMPOSITION AND THE PROCESS FOR ITS PREPARATION

(75) Inventors: Helle Weibel, Hillerod (DK); Thyge Borup Hjorth, Farum (DK)

(73) Assignees: Novo Nordisk A/S, Bagsvaerd (DK); Dr. Reddy's Research Foundation, Hyderabad (IN)

( * ) Notice: Subject to any disclaimer, the term of this patent is extended or adjusted under 35 U.S.C. 154(b) by 0 days.

(21) Appl. No.: 09/863,986

(22) Filed: May 23, 2001

(65) Prior Publication Data

US 2002/0010187 A1 Jan. 24, 2002

Related U.S. Application Data

(63) Continuation of application No. PCT/DK00/00291, filed on May 30, 2000, and a continuation-in-part of application No. 09/578,887, filed on May 26, 2000, now abandoned.
(60) Provisional application No. 60/207,888, filed on May 30, 2000.

(30) Foreign Application Priority Data

May 30, 2000  (WO) .............................. PCT/DK00/00291

(51) Int. Cl.[7] ........................ A61K 31/505; A61K 9/20; A61K 9/14

(52) U.S. Cl. .................... 514/259; 424/465; 424/489
(58) Field of Search ........................... 514/259; 424/465, 424/489

(56) References Cited

U.S. PATENT DOCUMENTS 5,480,652 A    1/1996   Bru-Magntez et al. ...... 424/466

FOREIGN PATENT DOCUMENTS

| EP | 0 945 134 A1 | 9/1999 |
| WO | 95/06461 | 3/1995 |
| WO | 96/18386 | 6/1996 |
| WO | 96/34606 | 11/1996 |
| WO | 97/41097 | 11/1997 |
| WO | 00/32191 | 6/2000 |

OTHER PUBLICATIONS

Biosis An 1989:475692, Aly et al, Acta Pharm Fenn, 1989, 98(1), 21–32, abstract.*

* cited by examiner

Primary Examiner—Rebecca Cook
(74) Attorney, Agent, or Firm—Reza Green

(57) ABSTRACT

The present invention provides a new stable pharmaceutical composition containing 5-[[4-[3-methyl-4-oxo-3,4-dihydro-2-quinazolinyl]methoxy]phenylmethyl]thiazolidine-2,4-dione as active ingredient.

18 Claims, No Drawings

1

PHARMACEUTICAL COMPOSITION AND THE PROCESS FOR ITS PREPARATION

CROSS REFERENCE TO RELATED APPLICATIONS

This application claims priority under 35 U.S.C. 119 of U.S. provisional application No. 60/207,888 filed May 30, 2000 and is a continuation under 35 U.S.C. 120 of U.S. patent application Ser. No. 09/578,887 filed May 26, 2000 abandoned and International Patent Application PCT/DK00/00291 filed May 30, 2000, the contents of which are fully incorporated herein by reference.

BACKGROUND

The subject-matter of the present invention is a new pharmaceutical composition containing 5-[[4-[3-methyl-4-oxo-3,4-dihydro-2-quinazolinyl]methoxy]phenylmethyl]thiazolidine-2,4-dione as active ingredient and the process for its preparation.

5-[[4-[3-Methyl-4-oxo-3,4-dihydro-2-quinazolinyl]methoxy]phenylmethyl]thiazolidine-2,4-dione and pharmaceutically acceptable salts thereof have been found useful in the treatment of type 2 diabetes acting as a insulin sensitizer as disclosed in PCT Publication WO 97/41097.

The active ingredient is present as the base or as a pharmaceutically acceptable salt, preferably as the potassium salt.

Various solutions have been proposed for the preparation of medications based on 5-[[4-[3-methyl-4-oxo-3,4-dihydro-2-quinazolinyl]methoxy]phenylmethyl]thiazolidine-2,4-dione.

BRIEF DESCRIPTION OF THE INVENTION

The aim of the present invention is to provide a new composition intended for the preparation of 5-[[4-[3-methyl-4-oxo-3,4-dihydro-2-quinazolinyl]methoxy]phenylmethyl]thiazolidine-2,4-dione with improved stability, in particular solid dosage forms thereof.

It has been found in fact that 5-[[4-[3-methyl-4-oxo-3,4-dihydro-2-quinazolinyl]methoxy]-phenylmethyl]thiazolidine-2,4-dione and its pharmaceutically acceptable salts may decompose in the presence of and in contact with water. Further it has been observed that decomposing may occur in the presence of oxygen.

Thus, from a first aspect, the subject-matter of the present invention is a pharmaceutical composition intended for the preparation of dosage forms and in particular solid dosage forms containing an efficacious quantity of 5-[[4-[3-methyl-4-oxo-3,4-dihydro-2-quinazolinyl]-methoxy]phenylmethyl]thiazolidine-2,4-dione or of one of its pharmaceutically acceptable salts as active ingredient.

The present invention is based on the surprising discovery of the fact that the stability of 5-[[4-[3-methyl-4-oxo-3,4-dihydro-2-quinazolinyl]methoxy]phenylmethyl]thiazolidine-2,4-dione, or of one of its pharmaceutically acceptable salts, can be considerably improved in preparations containing 5-[[4-[3-methyl-4-oxo-3,4-dihydro-2-quinazolinyl]methoxy]phenyl-methyl]thiazolidine-2,4-dione or of its pharmaceutically acceptable salts and antioxidant agent if the product is composed of excipients which do not contain water.

In another embodiment of the present invention, the pharmaceutical composition does not contain an antioxidant agent.

DETAILED DESCRIPTION

Pharmaceutically acceptable salts forming part of this invention include salts such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, aluminium salts. Salts may include acid addition salts where appropriate which are, sulphates, nitrates, phosphates, perchlorates, borates, hydrohalides, acetates, tartrates, maleates, citrates, succinates, palmoates, methane-sulpionates, benzoates, salicylates, hydroxynaphthoates, benzenesulfonates, ascorbates, glycerophosphates, ketoglutarates and the like.

5-[[4-[3-Methyl-4-oxo-3,4-dihydro-2-quinazolinyl]methoxy]phenylmethyl]thiazolidine-2,4-dione, together with a conventional adjuvant, antioxidant carrier, or diluent, and if desired a pharmaceutically acceptable acid addition salt thereof, may be placed into the form of pharmaceutical compositions and unit dosages thereof, and in such form may be employed as solids, such as tablets or filled capsules, or oral powders to be diluted immediately before use filled with the same, all for oral use, in the form of suppositories for rectal administration; or as pessaries for vaginal use; or in the form of sterile injectable powders for parenteral, transdermal, nasal, pulmonary and ocular use.

Within the framework of the present description and of the claims, by powders is meant any mixture of components, granulated or not, intended to be placed in solution and/or in suspension in water, or again to be ingested directly or by any other appropriate means as for example in a mixture with a food product.

In accordance with a particular characteristic of the invention, the manufacture of tablets is carried out as a direct compression.

In accordance with another particular characteristic, this composition also contains pharmaceutically acceptable excipients.

In accordance with a particular characteristic of the invention, the antioxidant agent cited above is selected from among α-tocopherol, γ-tocopherol, δ-tocopherol, extracts of natural origin rich in tocopherol, L-ascorbic acid and its sodium or calcium salts, ascorbyl palmitate, propyl gallate (PG), octyl gallate, dodecyl gallate, butylated hydroxy anisole (BHA) and butylated hydroxy toluene (BHT).

In accordance with a currently preferred embodiment, the antioxidant agent will be α-tocopherol.

In accordance with another particular characteristic of the invention, the diluent is lactose and/or cellulose microcrystalline, magnesium stearate, talc. However, any other pharmaceutically acceptable diluents could be used if the diluents have low water content. The quantities of diluents can be easily determined by a person skilled in the art and depend of course on the final pharmaceutical form required.

Generally speaking, a composition which complies with the present invention and which are intended for the preparation of tablets, may contain, expressed in parts by weight per 100 parts of 5-[[4-[3-methyl-4-oxo-3,4-dihydro-2-quinazolinyl]methoxy]phenyl-methyl]thiazolidine-2,4-dione, or of one of its pharmaceutically acceptable salts:

between 100 and 400,000 parts by weight of anhydrous lactose;

between 1 and 100 parts by weight of an antioxidant;

between 50 and 500 parts by weight of pregelatinized starch;

between 1000 and 10,000 parts by weight of microcrystalline cellulose;
between 10 and 500 parts by weight of crospovidone;
between 10 and 500 parts by weight of silicon dioxide;
between 10 and 500 parts by weight of hydrogenated vegetable oil;
between 10 and 500 parts by weight of magnesium stearate;
between 10 and 500 parts by weight of hydroxypropyl methylcellulose;
between 10 and 500 parts by weight of hydroxypropyl cellulose;
between 1000 and 10,000 parts by weight of mannitol;
between 10 and 500 parts by weight of stearic acid; or
between 10 and 500 parts by weight of titanium dioxide.

According to a preferred embodiment of the invention the water content of the excipients is very low. More specifically the water content in the diluents is very low in order to minimize the water content of the pharmaceutical composition. Lactose is used in its anhydrous form. Furthermore, all excipients may be applied in a dry form.

A convenient way of preparing the composition according to the present invention is only to use starting materials (excipients) having a low content of water. Preferably all starting materials used for the preparation of the composition according to the present invention should have a water content below about 1%, preferably below about 0.5%, more preferred below about 0.1%, and even more preferred below about 0.05%, (weight/weight).

Preferably, the composition according to the present invention should have a water content below about 1%, preferably below about 0.5%, more preferred below about 0.1%, (weight/weight).

In accordance with a second aspect, the subject-matter of the present invention is a pharmaceutical preparation, in the form of tablet or powder, characterised in that it contains a composition as defined previously associated if required with at least one customary additive selected from among the sweeteners, flavouring agents, colors and lubricants. A person skilled in the art can easily determine the choice of these additives and their quantity.

Another manufacturing process for pharmaceutical compositions according to the invention is mixing of 5-[[4-[3-methyl-4-oxo-3,4-dihydro-2-quinazolinyl]methoxy]phenylmethyl]thiazolidine-2,4-dione, one or more antioxidants and other pharmaceutical excipients followed by melt granulation in a high shear mixer. Hydrogenated, vegetable oil, waxes or other low temperature melting binders can be used. The granules can be filled into capsules, compressed into tablets or used in other pharmaceutical dosage forms.

More preferably the manufacturing process applied is direct compression of tablets, wherein 5-[[4-[3-methyl-4-oxo-3,4-dihydro-2-quinazolinyl]methoxy]phenylmethyl]thiazolidine-2,4-dione, one or more antioxidants and other excipients suitable for direct compression are mixed followed by tabletting.

Yet, another preferred embodiment of the manufacturing process is wet granulation, where granules are obtained by wet massing of 5-[[4-[3-methyl-4-oxo-3,4-dihydro-2-quinazolinyl]methoxy]phenylmethyl]thiazolidine-2,4-dione, together with one or more anti-oxidants and other excipients.

It is assumed that the contact time with water has to be very short.

The most preferred process comprises the direct compression whereby 5-[[4-[3-methyl-4-oxo-3,4-dihydro-2-quinazolinyl]methoxy]phenylmethyl]thiazolidine-2,4-dione is kept at conditions of low water vapour pressure.

A sweetener may be a natural sugar such as sorbitol or a synthetic product such as saccharine or aspartame.

When the antioxidant selected is ascorbylpalmitat, propylgallat, which is a powder, it can be advantageous to mix it in an appropriate excipient such as α-tocopherol succinat, lactose or cellulose micrycrystalline.

5-[[4-[3-Methyl-4-oxo-3,4-dihydro-2-quinazolinyl]methoxy]phenylmethyl]thiazolidine-2,4-dione has the formula:

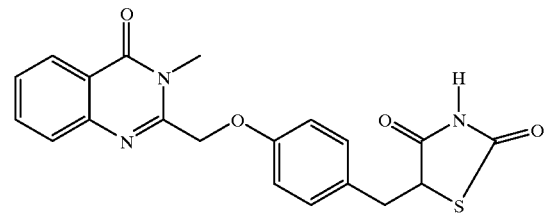

The present invention will further be illustrated with the following non-exhaustive examples.

EXAMPLES

In Example 1 through 4 the tablets were prepared according to the following procedure:

The active ingredient is mixed with cellulose microcrystalline in a drum mixer for 10 minutes. Lactose is added and the mixing continued for further two minutes. The lubricants are added and the mixing continued for further two minutes.

Example 1

25 mg 5-[[4-[3-methyl-4-oxo-3,4-dihydro-2-quinazolinyl]methoxyl]phenylmethyl]thiazolidine-2,4-dione, potassium salt Tablets 807227
5-[[4-[3-Methyl-4-oxo-3,4-dihydro-2-quinazolinyl]methoxy]phenylmethyl]thiazolidine-2,4-dione, potassium salt, 003/97 9%
Cellulose Microcrystalline 20%
Lactose 66%
Magnesium Stearate 0.5%
Talc 4.5%

Example 2

50 mg 5-[[4-[3-methyl-4-oxo-3,4-dihydro-2-quinazolinyl]methoxy]phenylmethyl]thiazolidine-2,4-dione, potassium salt tablets 807237
5-[[4-[3-Methyl-4-oxo-3,4-dihydro-2-quinazolinyl]methoxy]phenylmethyl]thiazolidine-2,4-dione, potassium salt, 003/97 18%
Cellulose Microcrystalline 20%
Mannitol 57%
Magnesium Stearate 0.5%
Talc 4.5%

Example 3

50 mg 5-[[4-[3-methyl-4-oxo-3,4-dihydro-2-quinazolinyl]methoxy]phenylmethyl]thiazolidine-2,4-dione, potassium salt Tablets 731725
5-[[4-[3-Methyl-4-oxo-3,4-dihydro-2-quinazolinyl]methoxy]phenylmethyl]thiazolidine-2,4-dione, potassium salt 18%
Lactose 81.5%
Magnesium stearate 0.5%

Example 4

0.25 mg 5-[[4-[3-methyl-4-oxo-3,4-dihydro-2-quinazolinyl]methoxy]phenylmethyl]thiazolidine-2,4-dione, potassium salt Tablets 728625

5-[[4-[3-Methyl-4-oxo-3,4-dihydro-2-quinazolinyl]
methoxy]phenylmethyl]thiazolidine-2,4-dione, potassium
salt 0.09%
  Mannitol 98%
  Magnesium stearate 2%

Example 5

5-[[4-[3-Methyl-4-oxo-3,4-dihydro-2-quinazolinyl]
methoxy]phenylmethyl]thiazolidine-2,4-dione, potassium
salt 0.09%
  Hydrogenated vegetable oil 6.25%
  Talc 5%
  α-tocopherol 50% of 5-[[4-[3-methyl-4-oxo-3,4-dihydro-2-quinazolinyl]methoxy]phenylmethyl]thiazolidine-2,4-dione, potassium salt
  Lactose DCL21Mannitol Up to 200 g The granulate is manufactured in a Baker Perkins 1 L high-shear mixer—using a water bath of 70° C. The mixing is carried out at 3000 RPM, chopper 6000 RPM and the granulation is performed at approx. 70° C. The hot granulate is sieved through sieve 1.25 μm, and the cold granulate through sieve 1000 μm. The glidant is added with a card for 2 min. The tablets are manufactured using a Diaf tablet machine with 9 mm punch. In order to protect against light and improve the appearance of the tablets, the tablets are film-coated.

The tablets were coated with the following film-coating composition where an amount of coating material of 5 mg/cm² were chosen as being satisfactory with respect to stability of the tablets:
  Methylhydroxypropylcellulose, Ph. Eur. ~4.34 mg/tablet
  Titanium Dioxide, Ph. Eur. ~1.73-
  Purified Water, Ph. Eur. q.s.-
  Talc, Ph. Eur. (Added as polishing agent at the end of the film-coating process (0.5% w/w of tablet core). Absorbed amount is not quantified.

Example 6

5-[[4-[3-Methyl-4-oxo-3,4-dihydro-2-quinazolinyl]
methoxy]phenylmethyl]thiazolidine-2,4-dione, potassium
salt 0.09%
  Povidone 7.5%
  Hydroxypropylmethyl cellulose 1.5%
  Croscarmelose sodium 1.56%
  Talc 1.1%
  Magnesium stearate 0.5%
  Lactose 300 mesh up to 200 g The granulate is manufactured by Baker Perkins 1 L intensive mixer. Dry mixing were carried out at 500 RPM, chopper 1500 RPM and granulation 1000 RPM and 2000 RPM. The wet granulate is sieved through sieve 1.25 μm and the dry granulate through sieve 1000 μm. The glidant is admixed with a card for 2 min. The tablets are manufactured by Diaf tablet machine with 9 mm punch.

Example 7

Composition: Oral Powder, 1 mg/ml, 100 ml
5-[[4-[3-Methyl-4-oxo-3,4-dihydro-2-quinazolinyl]
methoxy]phenylmethyl]thiazolidine-2,4-dione potassium
salt 0.1096 g
  Mannitol 2.5 g
  Hydroxypropyl-β-cyclodextrin 10 g
  To be diluted with 92 mL water before use.

Example 8

Composition: Oral Powder, 10 mg/ml, 100 ml
5-[[4-[3-Methyl-4-oxo-3,4-dihydro-2-quinazolinyl]
methoxy]phenylmethyl]thiazolidine-2,4-dion potassium salt
1.096 g
  Mannitol 2.5 g
  Hydroxypropyl-β-cyclodextrin 10 g
  Sodium Carbonate, anhydrous,
  $Na_2CO_3$ 15 mg
  To be diluted with 92 mL water before use.

What is claimed is:

1. A process for preparing a pharmaceutical composition, said process comprising forming a mixtute between (i) a compound selected from the group consisting of 5-[[4-[3-methyl-4-oxo-3,4-dihydro-2-quinazolinyl]methoxy]phenylmethyl]thiazolidine-2,4-dione and a pharmaceutically acceptable salt thereof, and (ii) one or more of a pharmaceutically acceptable carrier or excipient, wherein said mixture has a water content below about 1% (w/w).

2. The process of claim 1, wherein said pharmaceutically acceptable excipient comprises an antioxidant.

3. The process of claim 1, wherein said mixture further comprises a pharmaceutically acceptable excipient selected from the group consisting of:
  between 100 and 400,000 parts by weight of anhydrous lactose,
  between 1 and 100 parts by weight of an antioxidant,
  between 50 and 500 parts by weight of pregelatinized starch,
  between 1000 and 10,000 parts by weight of microcrystalline cellulose,
  between 10 and 500 parts by weight of crospovidone,
  between 10 and 500 parts by weight of silicon dioxide,
  between 10 and 500 parts by weight of hydrogenated vegetable oil,
  between 10 and 500 parts by weight of magnesium stearate,
  between 10 and 500 ports by weight of hydroxypropyl methylcellulose,
  between 10 and 500 parts by weight of hydroxypropyl cellulose,
  between 1000 and 10,000 parts by weight of mannitol,
  between 10 and 500 parts by weight of stearic acid, or
  between 10 and 500 parts by weight of titanium dioxide.

4. The process of claim 1, wherein the pharmaceutically acceptable excipients, prior to formation of said mixture, have a water content below about 0.5% (w/w).

5. The process of claim 2, wherein the antioxidant is selected from the group consisting of: α-tocopherol, γ-tocopherol, δ-tocopherol, extracts of natural origin rich in tocopherol, L-ascorbic acid and its sodium or calcium salts, ascorbyl palmitate, propyl gallate (PG), octyl gallate, dodecyl guilate, butylated hydroxy anisole (BHA) and butylated hydroxy toluene (BHT).

6. The process of claim 5, wherein the antioxidant is α-tocopherol.

7. The process of claim 1, wherein said mixture further comprises at least one customary additive selected from among the sweeteners, flavouring agents, colours and lubricants.

8. The process of claim 1, wherein the mixture further comprises talc in an amount of about 0-10% (weight/weight).

9. The process of claim 1, wherein said mixture comprises, by weight:

5-[[4-[3-methyl-4-oxo-3,4-dihydro-2-quinazolinyl] methoxy]phenylmethyl]thiazolidine-2,4-dione, potassium salt 9% cellulose microcrystallline 20% lactose 66% magnesium Stearate 0.5% talc 4.5%.

10. The process of claim 1, wherein said mixture comprises, by weight

5-[[4-[3-methyl-4-oxo-3,4-dihydro-2-quinazolinyl] methoxy]phenylmethyl]thiaxolidine-2,4-dione, potassium salt 18% cellulose microcrystallline 20% mannitol 57% magnesium stearate 0.5% talc 4.5%.

11. The process of claim 1, wherein said mixture comprises, by weight:

5-[[4-[3-methyl-4-oxo-3,4-dihydro-2-quinazolinyl] methoxy]phenylmethyl]thiazolidine-2,4-diane, potassium salt 18% lactose 81.5% magnesium stearate 0.5%.

12. The process of claim 1, wherein said mixture comprises, by weight:

5-[[4-[3-methyl-4-oxo-3,4-dihydro-2-quinazolinyl] methoxy]phenylmethyl]thiazolidine-2,4-dione, potassium salt 0.09% mannitol 98% magnesium stearate 2%.

13. The process of claim 2, wherein said mixture comprises, by weight:

5-[[4-[3-methyl-4-oxo-3,4-dihydro-2-quinazolinyl] methoxy]phenylmethyl]thiazolidine-2,4-diane, potassium salt 0.09% hydrogenated vegetable oil 6.25% talc 5%

α-tocopherol 50% of 5-[[4-[3-methyl-4-oxo-3,4-dihydro-2-quinazolinyl]methoxy]phenylmethyl]thiazolidine-2,4-diodine, potassium salt lactose DCL21/mannitol Up to 200 g.

14. The process of claim 1, wherein said mixture comprises, by weight:

5-[[4-[3-methyl-4-oxo-3,4-dihydro-2-quinazolinyl] methoxy]phenylmethyl]thiazolidine-2,4-dione, potassium salt 0.09% povidone 7.5% hydroxypropylmethyl cellulose 1.5% croscarmelose sodium 1.56% talc 1.1% magnesium stearate 0.5% lactose 300 mesh up to 200 g.

15. The process of claim 1, wherein said mixture comprises, by weight:

5-[[4-[3-methyl-4-oxo-3,4-dihydro-2-quinazolinyl] methoxy]phenylmethyl]thiazolidine-2,4-dione, potassium salt 0.1096 g mannitol 2.5 g hydroxypropyl-β-cyclodextrin 10 g and diluted with 92 mL water before use.

16. The process of claim 1, wherein said mixture comprises, by weight:

5-[[4-[3-methyl-4-oxo-3,4-dihydro-2-quinazolinyl] methoxy]phenylmethyl]thiazolidine-2,4-dione, potassium scdt 1.096 g mannitol 2.5 g hydroxypropyl-β-cyclodextrin 10 g sodium carbonate, anhydrous, $Na_2CO_3$ 15 mg and diluted with 92 mL water before use.

17. The process of claim 1, wherein said water content is below about 0.1% (w/w).

18. The process of claim 17, wherein said water content is below about 0.05%.

* * * * *